United States Patent
Udell et al.

(10) Patent No.: US 6,806,259 B2
(45) Date of Patent: Oct. 19, 2004

(54) HYALURONIC ACID IN SOFT GEL FORM

(75) Inventors: Ronald G. Udell, Beverly Hills, CA (US); Yousry M. A. Naguib, Arcadia, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

(21) Appl. No.: 10/035,753

(22) Filed: Dec. 21, 2001

(65) Prior Publication Data

US 2003/0119781 A1 Jun. 26, 2003

(51) Int. Cl.$^7$ ............... A01N 43/04; A61K 31/715; A61K 9/64
(52) U.S. Cl. ............ 514/54; 514/62; 514/420; 514/427; 514/560; 536/55.1; 536/55.2; 536/55.3; 536/123.1; 424/451; 424/456
(58) Field of Search ............ 514/54, 62, 420, 514/427, 560; 536/55.1, 55.2, 55.3, 123.1; 424/451, 456, 476

(56) References Cited

U.S. PATENT DOCUMENTS

| | | | | |
|---|---|---|---|---|
| 4,443,459 A | * | 4/1984 | Yano et al. | |
| 5,811,410 A | * | 9/1998 | Falk et al. | |
| 5,989,535 A | * | 11/1999 | Nayak et al. | |
| 6,028,105 A | * | 2/2000 | Nigra | |
| 6,339,074 B1 | * | 1/2002 | Cialdi et al. | .......... 514/54 |

FOREIGN PATENT DOCUMENTS

JP    61000017    *    1/1986

* cited by examiner

Primary Examiner—James O. Wilson
Assistant Examiner—Traviss C. McIntosh, III
(74) Attorney, Agent, or Firm—Dorsey & Whitney LLP; Scott D. Rothenberger

(57) ABSTRACT

An orally administered soft gelatin formulation preparation of low molecular weight Hyaluronic Acid (HA) for use as a nutritional supplement to provide the primary benefit of internally causing the softening of the human skin.

3 Claims, No Drawings

HYALURONIC ACID IN SOFT GEL FORM

BACKGROUND OF THE INVENTION

1. Field of the Invention

The present invention concerns an orally administered preparation of a composition of Hyaluronic Acid (HA) for use as a nutritional supplement with benefits of softening the human skin.

2. Background of the Invention

Hyaluronic Acid is a naturally occurring high molecular weight polysaccharide having an empirical formula of $C_{14}H_{20}NNa_{11}$ where n>1000. It is accepted that Hyaluronic Acid (HA) comes from three principle sources, human umbilical cords, rooster combs, and certain bacterial cultures from group A and C hemolytic streptococci. Commercial sources for HA are generally from umbilical cords and rooster combs. The present invention is derived from rooster combs.

HA was first isolated by Karl Meyer in 1934. He derived the novel glycosoaminoglycan from the vitreous of bovine eyes. The substance contained a uronic acid and an amino sugar, but no sulfoesters. Meyer's discovery is frequently referred to as Hylauron in vivo and Hyaluronic Acid (HA) ex vivo. The precise chemical structure was determined 20 years later and classified as part of biologically active molecules known as glycosoaminoglycans (GAGs). GAGs are principally located in or on the cellular membrane or in the material between cells called the extracellular matrix (ECM).

GAGs are long, unbranched polysaccharides containing a repeating disaccharide unit. In the case of Hyaluronan this disaccharide consists of D-glucuronate and D-acetylglucosamine. GAGs are negatively charged, high molecular weight molecules that have several unique properties. Among them is high viscosity in solution. High viscosity yields low compressibility resulting in excellent lubrication and shock absorption, particularly for soft tissues and joints. HA polymers are comparatively very large (i.e., having high molecular weight in the range of 1 million to 4 million daltons in a highly polymerized preparation) and can displace a large volume of water making them the body's premier lubricators.

HA is found in many tissues of the body. It is present in particularly high concentrations in the synovial fluid that lubricates the joints, in heart valve tissue, in the fluids of the inner ear, in many layers of the skin, especially the dermis, and in the vitreous humor of the eyes.

The preparation HA from rooster combs and human umbilical cords for use in eye and joint applications is described in U.S. Pat. No. 4,141,973 to E. A. Balazs. This patent provides a detailed review of the technical literature describing the isolation, characterization and uses of HA. U.S. Pat. No. 4,303,676 also to E. A. Balazs describes the cosmetic formulations containing Hyaluronate fractions in various molecular weight ranges made from rooster combs. U.S. Pat. No. 4,328,803 to L. G. Pape describes the use of an ultra-pure Hyaluronic Acid salt utilized in eye surgery. The HA product used here was a sodium Hyaluronate salt available under the registered trademark HYARTIL.RTM from Pharmacia, Inc. and obtained in commercial quantities from rooster combs as well.

The purpose it has in each of these applications is slightly different, but all are based on the principles of cellular hydration and separation. The hydration provided by HA allows for the proper transfer of nutrition and elimination of waste. In a sense, cells are bathed in a framework of HA. This framework allows the exchange of not just nutrition, but also regulatory and communication chemicals through the space between cells. Until recently, it was thought that HA was largely inert, that it simply filled the space between cells. This space, called the extra cellular matrix (ECM) is filled with a ground substance. The ground substance is primarily HA.

As Meyer observed when discussing sulfoesters, HA is unique among the GAGs because it does not contain sulfate and is not bonded to proteins as a proteoglycan. It is, however, a component of proteoglycans in the ECM. This gives HA great flexibility in providing scalable structural integrity through visco-elastic support necessary for separation between tissues while facilitating immune functions or intercellular communication. HA in the ECM helps control tissue permeation, bacterial invasiveness, and macromolecular transport between cells. HA also plays an important role in mediating how cells of neighboring tissues interact and communicate.

The body's need for HA is great. Not only is it an important part of tissue structure, but it also provides active support and binding sites for intracellular interactions, acts as a buffer zone to protect cells, and forms part of the waste complexes that is frequently eliminated from tissues frequently. Because of this, HA is catabolized in many tissues and must be renewed constantly.

Certain cells such as chondrocytes in the cartilage and keratinocytes in the epidermis actively synthesize and catabolize HA throughout a person's life span. Hascall et al. has found that the half-life of an HA molecule to be normally 2–3 weeks, while the half-life in the epidermis is amazingly less than one day. This production decreases with a person's increased age. Any means of increasing the amount of HA in the body promises to have great benefits in improving the quality, elasticity, and function of the skin and joints. Till now, large/high molecular weight HA has been topically applied in cosmetic products and injected in medical preparations for joint health.

Other attempts take the form of supplementing with HA components, namely chondroitin and glucosamine. While these are both effective in helping to augment the functions of HA in the joints, they have not been proven to assist in the intercellular functions of HA nor do they affect HA levels directly as far as it is known.

SUMMARY OF THE INVENTION

One of the difficulties in trying to increase the amount of available HA in the body is the size of the molecule. The large polymeric structure that grants HA its uniqueness, makes it difficult to acquire from outside the body. These large structures simply cannot pass from the digestive system to the blood stream. As a result most exogenous supplementation use of HA has been in the form of injection or topical application.

The present invention concerns an orally administered soft gelatin formulation that contains 35 to 45 mg of HA derived from 400 to 430 mg of an extract containing a concentration of 9% HA. The name INJUV™ has been selected as the trademark for the soft gelatine form of the present invention. The soft gel form makes it stable in retaining the properties of HA and the small molecular weight produces a bioavailable product able to be absorbed through digestion.

Other features and advantages of the present invention will become more apparent from the following detailed

DETAILED DESCRIPTION OF THE PREFERRED EMBODIMENT

The present invention is a soft gelatin, ingestible formulation of Hyaluronic Acid with low molecular weight. The composition is an oral preparation of between 35 to 45 mg dosage of low molecular weight (preferably between 50,000 to 200,000 daltons) Hyaluronic Acid (HA) derived from 400 to 430 mg of an extract containing approximately 9% concentration of HA. Injuv™ is selected as the commercial name and trademark for the preferred embodiment or formulation of the present invention that can be placed in a soft gelatin capsule having a dosage of approximately 38 mg of low molecular weight HA that is derived from approximately 420 mg of an extract containing approximately 9% concentration of HA. The present invention provides an oral dose form of HA which uses an enzyme cleaving technique and takes naturally derived Hyaluronic Acid and breaks it down to lower molecular weight polymers capable of absorption thorough oral administration via a soft gelatin capsule. The product can be taken every day as a dietary supplement for an indefinite period of time with benefits of softening of the human skin.

The manufacturing process of the present invention is as follows:

Melt Beeswax in rice Bran Oil;

Heat to a minimum of 60 degrees Celsius;

Allow to cool to 30 degrees celsius and add Hyaluronic Acid;

Mix for a minimum of thirty minutes;

Ensure that the mixture is homogenous and that no air remains; and

Encapsulate mixture in soft gelatin capsule.

A variety of further modifications and improvements in and to the present invention will be apparent to persons skilled in the art. Accordingly, no limitation on the invention is intended by way of the foregoing description, except as set forth in the appended claims.

What is claimed is:

1. A method for skin softening, comprising oral administration of hyaluronic acid in the form of a soft gelatin capsule having a dosage of between 35 to 45 mg and a molecular weight between 50,000 and 200,000 daltons.

2. The method of claim 1, wherein the soft gelatin capsule further includes beeswax.

3. The method of claim 1, wherein the soft gelatin capsule further includes rice bran oil.

* * * * *